United States Patent
Llorens-Cortes et al.

(10) Patent No.: US 10,959,938 B2
(45) Date of Patent: Mar. 30, 2021

(54) COMBINATION OF (3S,3S') 4,4'-DISULFANEDIYLBIS(3-AMINOBUTANE 1-SULFONIC ACID) AND A SECOND ANTIHYPERTENSIVE AGENT

(71) Applicants: QUANTUM GENOMICS, Massy (FR); INSERM (Institut National de la Santé et de la Recherche Médicale), Paris (FR)

(72) Inventors: Catherine Llorens-Cortes, Burse sur Yvette (FR); Yannick Marc, Paris (FR); Ji Gao-Desliens, Rosny sur Seine (FR); Fabrice Balavoine, Paris (FR); Lionel Segard, Massy (FR)

(73) Assignee: Quantum Genomics, Massy (FR)

( * ) Notice: Subject to any disclaimer, the term of this patent is extended or adjusted under 35 U.S.C. 154(b) by 0 days.

(21) Appl. No.: 14/367,408

(22) PCT Filed: Dec. 21, 2012

(86) PCT No.: PCT/EP2012/706607
§ 371 (c)(1),
(2) Date: Jun. 20, 2014

(87) PCT Pub. No.: WO2013/092984
PCT Pub. Date: Jun. 27, 2013

(65) Prior Publication Data
US 2015/0320703 A1 Nov. 12, 2015

(30) Foreign Application Priority Data
Dec. 21, 2011 (EP) .................................... 11306735

(51) Int. Cl.
| | | |
|---|---|---|
| A61K 31/185 | (2006.01) |
| A61K 9/00 | (2006.01) |
| A61K 31/4178 | (2006.01) |
| A61K 31/567 | (2006.01) |
| A61P 9/12 | (2006.01) |
| A61K 31/4184 | (2006.01) |
| A61K 31/255 | (2006.01) |
| A61K 31/4704 | (2006.01) |
| A61K 38/00 | (2006.01) |
| A61K 31/403 | (2006.01) |
| A61K 31/41 | (2006.01) |
| A61K 38/05 | (2006.01) |
| A61K 31/401 | (2006.01) |
| A61K 45/06 | (2006.01) |
| A61K 35/74 | (2015.01) |

(52) U.S. Cl.
CPC .............. *A61K 9/00* (2013.01); *A61K 9/0053* (2013.01); *A61K 9/0095* (2013.01); *A61K 31/185* (2013.01); *A61K 31/255* (2013.01); *A61K 31/401* (2013.01); *A61K 31/403* (2013.01); *A61K 31/41* (2013.01); *A61K 31/4178* (2013.01); *A61K 31/4184* (2013.01); *A61K 31/4704* (2013.01); *A61K 31/567* (2013.01); *A61K 35/74* (2013.01); *A61K 38/00* (2013.01); *A61K 38/005* (2013.01); *A61K 38/05* (2013.01); *A61K 45/06* (2013.01); *A61P 9/12* (2018.01)

(58) Field of Classification Search
CPC .... A61K 31/185; A61K 38/05; A61K 38/005; A61K 9/0053; A61K 31/41
See application file for complete search history.

(56) References Cited

U.S. PATENT DOCUMENTS

| | | | |
|---|---|---|---|
| 6,340,708 B1 | 1/2002 | Llorens-Cortes et al. | |
| 7,235,687 B2 * | 6/2007 | Fournie-Zaluski | C07C 323/66 562/101 |
| 2006/0135602 A1 | 6/2006 | Fournie-Zaluski et al. | |
| 2006/0205695 A1 | 9/2006 | Roques et al. | |
| 2008/0014187 A1 * | 1/2008 | Villeponteau | A61K 31/401 424/94.1 |

OTHER PUBLICATIONS

Fournie-Zaluski et al., PNAS, May 18, 2004, vol. 101, No. 20, 7775-7780.*
Marc et al., Hypertension. 2012;60:411-418.*
Bodineau et al., Hypertension, 2008;51:1318-1325.*
Korzun et al., "Comparative characteristics of ACE inhibitors," Human Ecology (2003); 2:16-22.
Berenbaum, M.C., "What is Synergy," Pharmacological Reviews (1989); 41(2):93-141.

* cited by examiner

*Primary Examiner* — Robert S Cabral
(74) *Attorney, Agent, or Firm* — Fox Rothschild LLP (57) ABSTRACT

The present invention relates to a pharmaceutical composition comprising, in at least one pharmaceutically acceptable support or vehicle, a combination of (3S,3S')4,4'-disulfanediylbis(3-aminobutane 1-sulfonic acid) or a pharmaceutically acceptable salt or solvate thereof and a second active ingredient selected from the group consisting of angiotensin I converting enzyme inhibitors and angiotensin II receptor type I antagonists. Said composition is particularly useful for the treatment of hypertension and related diseases and conditions.

4 Claims, 4 Drawing Sheets

COMBINATION OF (3S,3S') 4,4'-DISULFANEDIYLBIS(3-AMINOBUTANE 1-SULFONIC ACID) AND A SECOND ANTIHYPERTENSIVE AGENT

FIELD OF THE INVENTION

The present invention relates to a pharmaceutical composition comprising, in at least one pharmaceutically acceptable support or vehicle, a combination of (3S,3S') 4,4'-disulfanediylbis(3-aminobutane 1-sulfonic acid) or a pharmaceutically acceptable salt or solvate thereof and a second active ingredient selected from the group consisting of angiotensin I converting enzyme (EC 3.4.15.1) inhibitors (ACEIs) and angiotensin II receptor type 1 (AT1R) antagonists. Said composition is particularly useful for the treatment of hypertension and related diseases and conditions.

TECHNICAL BACKGROUND

Hypertension is an arterial disorder whose causes generally remain unknown. Extrinsic factors which may participate include obesity, sedentary lifestyle, excessive alcohol or salt intake, and stress. Intrinsic factors suggested to play a role include fluid retention, sympathetic nervous system activity and constriction of blood vessels. Arterial hypertension can contribute directly or indirectly to diseases of the heart, the peripheral and cerebral vascular system, the brain, the eye and the kidney. Glycemic control and/or Blood Pressure (BP) lowering are the main treatment strategies for prevention of diabetic complications, e.g., nephropathy, retinopathy and neuropathy.

Antihypertensive agents have been widely used for the treatment of hypertension and related diseases and conditions.

Despite the availability of more than 75 antihypertensive agents, BP control and its concomitant risk factors in the general population remains difficult to control. Indeed, 65% of patients diagnosed with hypertension do not have their high BP controlled (<140/90 mmHg). Many patients will require more than one drug to successfully achieve their target BP level and in many cases combinations of two or even three drugs are prescribed. The current antihypertensive drugs are also less effective in patients of African ancestry or with diabetes mellitus or renal insufficiency in whom high BP is associated with low plasma renin levels and high plasma arginine-vasopressin (AVP) levels. Finally, the overall incidence of resistant hypertension to at least three antihypertensive drugs (including a diuretic) is estimated to be 15% of the hypertensive population. Consequently, there is an unmet medical need to develop new antihypertensive therapies with different mechanisms of action, as alternative or complementary therapies to improve furthermore BP control and the associated cardiovascular risks in patients.

Antihypertensive drugs lower blood pressure BP, although the mechanisms of action among this diverse group vary greatly. Within this therapeutic class, there are several subgroups, which comprises a very large number of drugs, among them the drugs listed below which are representatives but not the only members of their classes. Treatment of arterial hypertension includes the use of thiazide diuretic agents, beta-adrenergic blockers ("beta blockers"), alpha/beta adrenergic blockers, non-specific adrenergic blocking agents, angiotensin converting enzyme inhibitors (ACEIs), AT1R antagonists (or angiotensin II receptor type 1 blockers [ARBs]), calcium channel antagonists or blockers (GCBs) and direct vasodilators.

The thiazide diuretics include chlorothiazide, hydrochlorothiazide (or HCTZ), chlorthalidone, indapamide, polythiazide, and hydroflumethiazide. The drugs in this class lower BP through several mechanisms. By promoting sodium loss, they lower blood volume. At the same time, the pressure of the walls of blood vessels, the peripheral vascular resistance, is lowered. Thiazide diuretics are commonly used as the first choice for reduction of mild hypertension, and are commonly used in combination with other antihypertensive drugs. In particular, combinations of hydrochlorothiazide, and to a less extent chlorthalidone, with specific ACEIs, ARBs, beta blockers and other diuretics, are currently available combination drugs for antihypertension.

It is desirable to identify further combinations to treat arterial hypertension.

ACEIs act by inhibiting the production of angiotensin II, a peptide substance that by acting on AT1 receptors both induces constriction of blood vessels and sodium retention, which leads to water retention and increased blood volume. There are many ACEIs currently available in the market, including captopril, ramipril, quinapril, enalapril, perindopril and benazepril. The primary difference between these drugs is their onset and duration of action.

The ARBs, such as losartan, candesartan, irbesartan, telmisartan, valsartan, olmesartan and eprosartan, block the action of angiotensin II on AT1 receptors rather than blocking its production (like ACEIs).

ACEIs and ARBs thus target the systemic renin-angiotensin system (RAS) and more specifically angiotensin II, either by preventing its formation through ACE inhibition or by preventing angiotensin II from binding to AT1 receptors. In both cases, inhibition leads to vasodilatation and reduction in BP. Recent evidences support that a functional RAS, controlling cardiovascular functions and body fluid homeostasis, is also present in the brain (Llorens-Cortes C. and Mendelsohn F A. Organisation and functional role of the brain angiotensin system. J Renin Angiotensin Aldosterone Syst 2002 September; 3 Suppl 1:S39-S48). Hyperactivity of the brain RAS and particularly of aminopeptidase A (APA), a membrane-bound zinc metalloproteases involved in vivo in the conversion of brain angiotensin II (AngII) and to angiotensin III (AngIII) (Zini et al PNAS 1996) respectively, plays a critical role in mediating hypertension in various animal models of hypertension (Marc Y. and Llorens-Cortes C. The role of the brain renin-angiotensin system in hypertension: Implications for new treatment. Prog Neurobiol. 2011 Jul. 7; 95(2):89-103).

Several studies pointed out that in the brain, AngIII and not Ang II as established at the periphery, constitutes one of the major effector peptides of the brain RAS in the control of BP and AVP release (Zini et al PNAS 1996, Reaux et al PNAS 1999). Furthermore brain AngIII exerts a tonic stimulatory action on the control of BP in hypertensive animals (Reaux at al PNAS 1999, Fournie-Zaluski et al PNAS 2004). Therefore, brain APA, the enzyme generating AngIII in the brain RAS, constitutes a relevant therapeutic target for treatment of arterial hypertension and centrally active APA inhibitors represent a new class of antihypertensive agents. Among these novel antihypertensive agents, one can cite in particular (3S,3S') 4,4'-disulfanediylbis(3-aminobutane 1-sulfonic acid) that is a prodrug of the selective aminopeptidase A (APA) inhibitor 3-amino 4-mercaptobutanesulfonic acid (also called EC33).

Besides improving BP control in treated hypertensive patients with the available armamentarium of drugs, epidemiological studies support the need of developing new classes of antihypertensive drugs like (3S,3S') 4,4'-disulfanediylbis(3-aminobutane 1-sulfonic acid) and new combinations of drugs which can interfere with the mechanisms involved in the genesis and maintenance of elevated BP in uncontrolled and/or resistant patients, present reduced side-effects compared to the existing treatments and reduce the associated risks of cardiovascular diseases such as myocardial infarction, cardiac arrest, stroke, or renal dysfunction.

SUMMARY OF THE INVENTION

The inventors identified a very promising combination of drugs allowing a significant hypotensive effect. More particularly, this significant hypotensive effect occurs early after concomitant oral administration of both antihypertensive agents (in particular, less than two hours) and is maintained in a satisfactory manner.

In one embodiment, the present invention relates to a pharmaceutical composition, comprising in at least one pharmaceutically acceptable support or vehicle a combination of (3S,3S') 4,4'-disulfanediylbis(3-aminobutane 1-sulfonic acid) or a pharmaceutically acceptable salt or solvate thereof and a second active ingredient selected from the group consisting of ACEIs and ARBs.

Said composition is particularly useful for the treatment of arterial hypertension or indirectly or directly related diseases.

In accordance with another embodiment of the present invention, a method is disclosed for the treatment of hypertension and indirectly or directly related diseases. The method and use of the invention comprises administering to a subject in need of such treatment an effective amount of a pharmaceutical composition comprising, in at least one pharmaceutically acceptable support or vehicle, a combination of (3S,3S') 4,4'-disulfanediylbis(3-aminobutane 1-sulfonic acid) or a pharmaceutically acceptable salt or solvate thereof and a second active ingredient selected from the group consisting of ACEIs and ARBs.

DESCRIPTION OF THE INVENTION

The ACEIs include more particularly lisinopril, enalapril, quinapril, ramipril, benazepril, captopril, cilazapril, fosinopril, imidapril, moexipril, trandolapril, and perindopril. According to a preferred embodiment, the ACEI is selected from the group consisting of enalapril, captopril, ramipril, and quinapril. More specifically, the ACEI is enalapril.

The ARBs include more particularly losartan, candesartan, irbesartan, telmisartan, valsartan, olmesartan and eprosartan. According to a preferred embodiment, the ARB is selected from the group consisting of losartan, candesartan, valsartan and olmesartan. More specifically, the ARB is valsartan.

(3S,3S') 4,4'-disulfanediylbis(3-aminobutane 1-sulfonic acid) is a dimer of the selective aminopeptidase A (APA) inhibitor 3-amino 4-mercaptobutanesulfonic acid (also called EC33), generated by creating a disulfide bond between thiol groups of two 3-amino 4-mercaptobutanesulfonic acid molecules. Dimerisation affords a molecule more amenable to cross the gastro-intestinal and blood-brain barriers as a prodrug. (3S,3S') 4,4'-disulfanediylbis(3-aminobutane 1-sulfonic acid) (also called RB150) has been proven to be an efficient anti-hypertensive agent, as described by Fournie-Zaluski et al PNAS 2004 and Bodineau et al. in Hypertension 2008 51, 1318-1325.

(3S,3S') 4,4'-disulfanediylbis(3-aminobutane 1-sulfonic acid) and use thereof as anti-hypertensive agent have been disclosed in the patent application WO2004/007441.

A pharmaceutically acceptable salt or solvate thereof can also be used.

Indeed, organic compounds can form complexes with solvents in which they are reacted or from which they are precipitated or crystallized. These complexes are known as "solvates". For example, a complex with water is known as a "hydrate". Solvates of (3S,3S') 4,4'-disulfanediylbis(3-aminobutane 1-sulfonic acid) are within the scope of the present invention. Organic compounds can exist in more than one crystalline form. For example, crystalline form may vary from solvate to solvate. Thus, all crystalline forms of (3S,3S') 4,4'-disulfanediylbis(3-aminobutane 1-sulfonic acid) or the pharmaceutically acceptable solvates thereof are within the scope of the present invention.

It will also be appreciated by the person skilled in the art that (3S,3S') 4,4'-disulfanediylbis(3-aminobutane 1-sulfonic acid) may also be utilized in the form of pharmaceutically acceptable salts thereof. The pharmaceutically acceptable salts of (3S,3S') 4,4'-disulfanediylbis(3-aminobutane 1-sulfonic acid) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic etc. Other acids such as oxalic, while not in themselves pharmaceutically acceptable, may be useful in the preparation of salts useful as intermediates in obtaining the compounds of the present invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to (3S,3S') 4,4'-disulfanediylbis(3-aminobutane 1-sulfonic acid) include the acid form and its pharmaceutically acceptable salts and solvates.

In preferred embodiments, the indirectly or directly diseases related to hypertension are selected from the group consisting of diseases of the heart, the peripheral and cerebral vascular system, the brain, the eye and the kidney. In particular, diseases include primary and secondary arterial hypertension, ictus, myocardial ischaemia, heart failure, renal failure, myocardial infarction, peripheral vascular disease, diabetic proteinuria, Syndrome X and glaucoma. It may also include more particularly nephropathy, retinopathy and neuropathy in hypertensive diabetic patients.

Within the context of the invention, the term treatment denotes curative, symptomatic, and preventive treatment. Compositions of the invention can be used in humans with existing hypertension. The compositions of the invention will not necessarily cure the patient who has hypertension but will control BP in a satisfactory manner delaying or slowing thereby the progression or preventing thereby further complications of hypertension such as the directly or indirectly diseases as mentioned above. This will ameliorate consequently the patients' condition. The compositions of the invention can also be administered to those who do not have indirectly or directly diseases yet but who would normally develop the diseases or be at increased risk for said diseases, they will not develop said diseases. Treatment also includes delaying the development of indirectly or directly diseases in an individual who will ultimately develop said diseases or would be at risk for the diseases due to age, familial history, genetic or chromosomal abnormalities. By delaying the onset of the indirectly or directly diseases, compositions of the invention have prevented the individual from getting the diseases during the period in which the individual would normally have gotten the diseases or reduce the rate of development of the diseases or some of its effects but for the administration of compositions of the invention up to the time the individual ultimately gets the diseases.

In treating the hypertension, the compositions of the invention are administered in a therapeutically effective amount.

In an aspect of the invention, the amounts of (3S,3S') 4,4'-disulfanediylbis(3-aminobutane 1-sulfonic acid) and the second antihypertensive agent are sufficient to produce a synergistic antihypertensive effect.

In a more preferred embodiment, the second antihypertensive agent is an ACEI as defined above.

The pharmaceutical compositions according to the present invention are useful in the treatment of hypertension or indirectly or directly related diseases.

The pharmaceutical compositions of the invention advantageously contain one or more supports or vehicles that are pharmaceutically acceptable. More preferably, the composition is intended for an oral administration, the pharmaceutically acceptable support or vehicle is thus suitable for an oral administration. As examples, mention may be made of saline, physiological, isotonic, buffered solutions, etc. compatible with pharmaceutical use and known to persons skilled in the art.

The pharmaceutical composition comprising the combination of both active ingredients, i.e., (3S,3S') 4,4'-disulfanediylbis(3-aminobutane 1-sulfonic acid) or a pharmaceutically acceptable salt or solvate thereof and a second active ingredient selected from the group consisting of ACEIs and ARBs, can be prepared by mixing together both active ingredients, either all together or independently, with a physiologically acceptable support, an excipient, a binder, or a diluent, etc. The pharmaceutical composition of the invention is more specifically for a simultaneous, separate or sequential administration, preferably for simultaneous administration, of said active ingredients.

The pharmaceutical composition is then administered orally or non-orally, for instance via the parenteral, intravenous, cutaneous, nasal, rectal route or via aerosol delivery to the lungs. If the active ingredients are formulated independently, the corresponding formulations can be mixed together extemporaneously, using for instance a diluent, and are then administered or can be administered independently of each other, either successively or sequentially.

Preferably, the composition of the invention is administered orally.

The pharmaceutical compositions of the invention include formulations, such as granules, powders, tablets, gel capsules, syrups, emulsions and suspensions, and also forms used for non-oral administration, for instance injec-tions, sprays or suppositories.

The pharmaceutical forms can be prepared via the known conventional techniques.

The preparation of an orally administered solid pharmaceutical form will be performed by the following process: an excipient (for example lactose, su-crose, starch, mannitol, etc.), a disintegrant (for example calcium carbonate, calcium carboxymethylcellulose, etc.), a binder (for example starch, gum arabic, carboxymethylcellulose, polyvinylpyrrolidone, hydroxypropylcellulose, etc.) and a lubricant (for example talc, magnesium stearate, etc.) are, for example, added to the active ingredient(s) and the mixture obtained is then tabletted. If necessary, the tablet can be coated via the known techniques, in order to mask the taste (for example with cocoa powder, mint, etc.) or to allow enteric dissolution or sustained release of the active ingredients. Pharmaceutically acceptable colorants may be added. Pharmaceutical forms, such as tablets, powders, sachets and gel capsules can be used for an oral administration.

The liquid pharmaceutical forms for oral administration include solutions, suspensions and emulsions. The aqueous solutions can be obtained by dis-solving the active ingredient(s) in water, followed by addition of flavourings, colorants, stabilisers and thickener, if necessary. In order to improve the solubility, it is possible to add ethanol, propylene glycol or other pharmaceutically acceptable non-aqueous solvents. The aqueous suspensions for oral use can be obtained by dispersing the finely divided active ingredient(s) in water with a viscous product, such as natural or synthetic gums, resins, methylcellulose or sodium carboxymethylcellulose.

The pharmaceutical forms for injection can be obtained, for example, by the following process. The active ingredient(s) is (are) dissolved, suspended or emulsified either in an aqueous medium (for example distilled water, physiological saline, Ringer's solution, etc.) or in an oily medium (for example a plant oil, such as olive oil, sesameseed oil, cottonseed oil, corn oil, etc., or propylene glycol), with a dispersant, a preserving agent, an isotonicity agent and also other additives, such as, if desired, a solubilising agent or a stabiliser.

A pharmaceutical form for external use can be obtained from a solid, semi-solid or liquid composition containing the active ingredients. For example, to obtain a solid form, the active ingredients are treated, alone or as mixtures, with excipients and a thickener so as to convert them into powder. The liquid pharmaceutical compositions are prepared in substantially the same way as the forms for injection, as indicated previously. The semi-solid pharmaceutical forms are preferably in the form of aqueous or oily gels or in the form of po-made. These compositions may optionally contain a pH regulator and also other additives.

A therapeutically effective amount (i.e., an effective dosage) of a composition or of active ingredients of the invention is determined by one skilled in the art. More specifically, an effective amount is an amount that allows decreasing and maintaining BP as to control BP, in particular BP goal of <140/90 mmHg is recommended. More preferably, the amounts of (3S,3S') 4,4'-disulfanediylbis(3-aminobutane 1-sulfonic acid) and the second antihypertensive agent are sufficient to produce a synergistic antihypertensive effect. The compositions of the invention can be administered at least once per week, but also once every day or every 2, 3, 4, 5 or 6 days.

Moreover, it will be appreciated that the amount of the active ingredients of the present invention required for use in treatment will vary with the nature of the condition being treated and the age and the condition of the subject and will be ultimately at the discretion of the attendant physician or veterinarian. In general, however, doses employed for adult human treatment will typically be in the range of 0.02-5000 mg per day or every other day, preferably 1-1500 mg per day or every other day, of (3S,3S') 4,4'-disulfanediylbis(3-aminobutane 1-sulfonic acid). With respect to the second antihypertensive agent, doses employed for adult human treatment will take into account the recommended dosages thereof. The desired dose may conveniently be presented in a single dose or as divided doses administered at appropriate intervals, for example as two, three, four or more sub-doses per day or every other day. The compositions according to the present invention may contain between 0.1-99% of each active ingredient, conveniently from 30-95% for tablets and capsules and 3-50% for liquid preparations.

The relative proportions of both active ingredients may vary upon the subject condition and also upon the second selected active ingredient. For example, the weight ratio of (3S,3S') 4,4'-disulfanediylbis(3-aminobutane 1-sulfonic acid) relative to enalapril may range between 10/1 and 300/1 and preferably from 25/1 to 200/1. The weight ratio of (3S,3S') 4,4'-disulfanediylbis(3-aminobutane 1-sulfonic acid) relative to valsartan may range between 5/1 and 500/1 and preferably from 10/1 to 200/1. The frequency of administration of the active ingredients of the invention is preferably between one and two administrations per day or every other day.

According to the invention, a subject can be a human being or an animal.

The aim of the present invention is also to propose a method or a composition as defined above where both active ingredients are coadministered. The present invention deals with a method or a composition as defined above of treatment via co-administration of effective amounts of (3S,3S') 4,4'-disulfanediylbis(3-aminobutane 1-sulfonic acid) or a pharmaceutically acceptable salt or solvate thereof and of a second active ingredient selected from the group consisting of ACEIs and ARBs, and also kits for allowing this co-administration.

The present invention also relates to kits that are suitable for the treatment by the methods described above. These kits comprise a composition containing (3S,3S') 4,4'-disulfanediylbis(3-aminobutane 1-sulfonic acid) or a pharmaceutically acceptable salt or solvate thereof and a second composition containing a second active ingredient selected from the group consisting of an ACEIs and ARBs, for a simultaneous, separate or sequential administration, preferably for simultaneous administration.

The pharmaceutical compositions can be included in a container, pack, or dispenser together with instructions for administration.

The term "co-administration" means the simultaneous, separate or sequential administration of both active ingredients to the same subject or patient, over a period that may be up to 2 hours or even up to 6 hours. For example, the term co-administration includes (1) a simultaneous administration of the two active ingredients, (2) an administration of the first, followed 2 hours later by the administration of the second active ingredient, (3) an administration of the first, followed 6 hours later by the administration of the second active ingredient.

According to a preferred embodiment, both active ingredients are simultaneously coadministered.

The examples below of compositions according to the invention are given as non-limiting illustrations.

EXAMPLES

The amounts are expressed on a weight basis, unless otherwise stated.

Materials and Methods

Active Ingredients

RB150, the ACEI, enalapril (supplied from Merck Sharp and Dohme research Lab), and the ARB, valsartan (Sigma-Aldrich), were dissolved in sterile saline and adjusted to pH 7.4 for in vivo administration.

Animals

Male spontaneously hypertensive rats (SHR), weighing 250 to 350 g, were obtained from Charles River Laboratories (L'Arbresle, France) and animals were kept under artificial light (12-hours light/12-hours dark cycle) with a normal standard diet and water given ad libitum. The experiments were conducted according to the National Institutes of Health Guide for the Care and Use of Laboratory Animals.

Surgical Methods and Blood Pressure Recording.

Twelve weeks male SHR were anesthetized with pentobarbital sodium (60 mg/kg, i.p, Centravet). Catheters were implanted in the femoral artery. The femoral arterial catheter was brought under the skin and emerged at the nape of the neck. After surgery, each rat was given an intraperitoneal injection of 0.1 mL of penicillin-streptomycin (50,000 units/mL; Sigma) and allowed to recover for at least 24 hours before the experiment. Typically, saline, RB150 (100 mg/kg) or enalapril (1 mg/kg) or valsartan (0.3 mg/kg) were orally administered (300 µL) in conscious, unrestrained rats. For example, to prepare the orally administered solution, RB150 plus enalapril, RB150 and enalapril were first diluted to respectively 15 mg/mL and 6 mg/mL in sterile saline. Then for a rat weighing 300 g, 0.05 mL of enalapril (6 mg/mL) was mixed with 2 mL of RB150 (15 mg/mL) and 2 mL of the final solution was given orally by gavage to SHR. After treatment, mean arterial blood pressure (MABP) and heart rate (HR) were monitored continuously for 6 h on the first day of experiment. Another recording of 1 hour was performed 24 hours after drug administration. Each experiment was monitored by using a COBE CDX III pressure transducer (Phymep, Paris, France) connected to the MacLab system (Phymep) consisting of a MacLab hardware unit and chart software running on a Macintosh computer. MABP and HR were calculated by the BP signal.

Data Analysis and Statistics

MABP and HR after RB150 oral administration were made with paired or unpaired Student's t test. A factorial two-way analysis of variance (ANOVA) was performed to test the interaction of time and treatment on the different variables of ΔMABP. The treated groups and the saline group within each treatment were compared at each time by a factorial 1-way ANOVA and Fisher PLSD test. Differences were considered significant if P value was <0.05.

Results

Effects of Concomitant Acute Oral Administration of RB150 with Enalapril on BP and HR in Freely Moving SHR.

Figure 1:
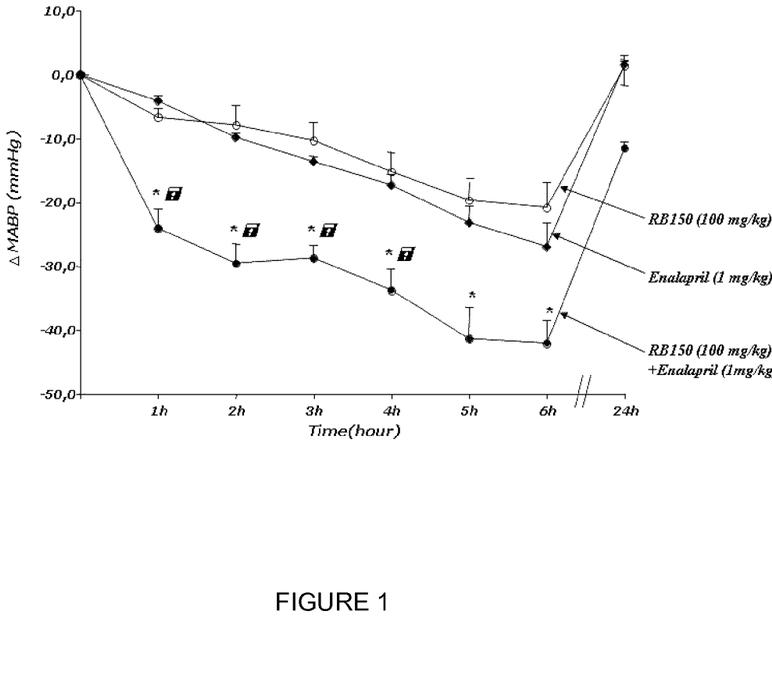
FIG. 1: Effects of RB150 and enalapril given alone or in combination by oral route on BP in alert SHRs (acute treatment)—■ p<0.05 vs RB150; * p<0.05 vs enalapril; n=4 for enalapril and enalapril+RB150, n>7 for RB150
Figure 2:
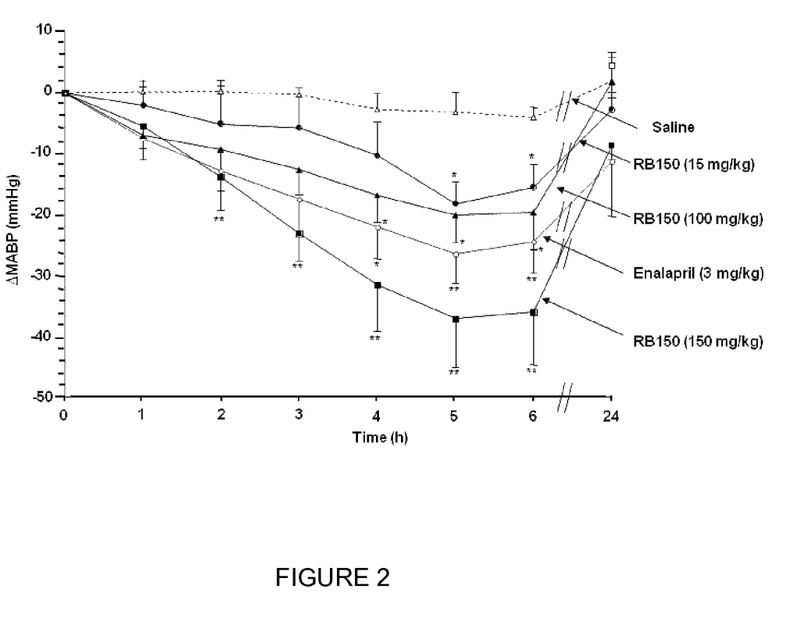
FIG. 2: Mean arterial blood pressure (MABP) changes in conscious SHR after oral RB150 or enalapril administration. Peak changes in mean arterial BP (ΔMABP in mmHg, mean±SEM) after acute oral RB150 administration (15-150 mg/kg) or enalapril (3 mg/kg) in conscious SHR (n=5 to 9 for each dose) at different times after drug administration (B). Unpaired Student's t test, * P<0.05;  P<0.01; * P<0.001 vs variation in corresponding MABP values obtained in SHR after oral administration of saline.

Concomitant oral administration of RB150 (100 mg/kg) with enalapril (1 mg/kg) significantly and markedly decreased MABP (FIG. 1) without altering significantly HR (not shown) in conscious SHR. The BP decrease (−24±2.9 mmHg) is already significant one hour after administration (FIG. 1). A maximal decrease in MABP (−42±3.6 mmHg) was observed 6 hours after administration. For each time, the hypotensive effect induced by the combination of RB150 (100 mg/kg, po) plus enalapril (1 mg/kg, po) was significantly different from the hypotensive effects of each compound administered alone. This was particularly illustrated one hour after administration. Indeed, even higher doses of RB150 (i.e. 150 mg/kg po) or enalapril (i.e. 3 mg/kg, po) alone did not induce any significant BP decrease in SHR, 1 hour after drug administration (FIG. 2).

Effects of Concomitant Acute Oral Administration of RB150 with Valsartan on BP and HR in Freely Moving SHR.

Figure 3:
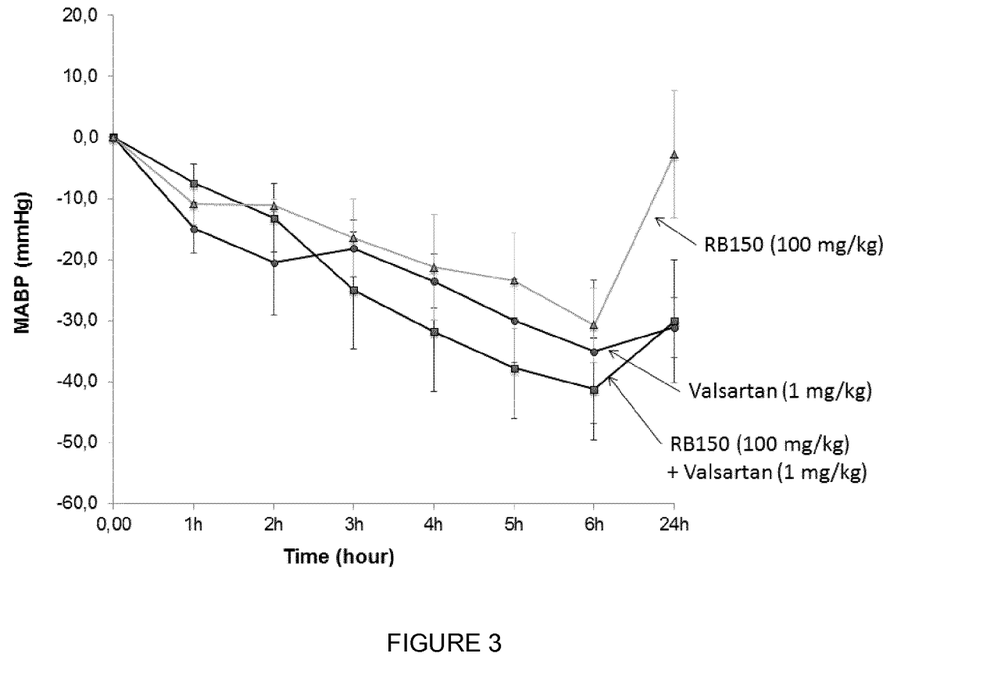
FIG. 3: Mean arterial blood pressure (MABP) changes in conscious SHR after acute oral administrations of RB150 (100 mg/kg) or valsartan (1 mg/kg) given alone or in combination. Peak changes in MABP (ΔMABP in mmHg, mean±SEM) at different times after drug administration (n=3 to 5 for each dose).
Figure 4:
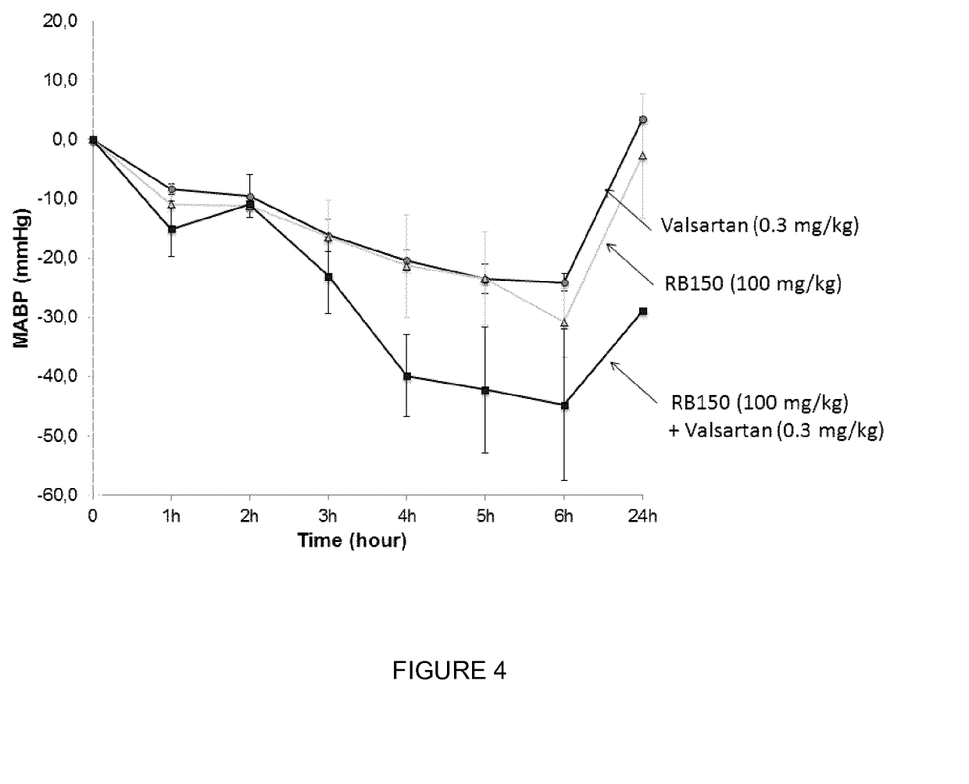
FIG. 4: Mean arterial blood pressure (MABP) changes in conscious SHR after acute oral administrations of RB150 (100 mg/kg) or valsartan (0.3 mg/kg) given alone or in combination. Peak changes in MABP (ΔMABP in mmHg, mean±SEM) at different times after drug administration (n=3 for each dose)

Concomitant oral administration of RB150 (100 mg/kg) with valsartan (1 mg/kg) markedly decreased MABP in conscious SHR (FIG. 3). However at this dose of valsartan, the decrease in BP induced by the combination is not significantly different from the decrease in BP induced by each compound administered alone. Interestingly, concomitant oral administration of RB150 (100 mg/kg) with a lower dose of valsartan (i.e. 0.3 mg/kg) also markedly decreased MABP in conscious SHR (FIG. 4). The maximal BP decrease (between −40 and −45 mmHg) is observed between 4 and 6 hours after administration. Between 4 and 6 hours after administration, the hypotensive effect induced by the combination of RB150 (100 mg/kg, po) and valsartan (0.3 mg/kg) was different from the hypotensive effects of each compound administered alone. This was particularly illustrated 4 hours after administration. This suggests that the combination of RB150 with valsartan could improve BP control while decreasing the doses of valsartan.

Formulation Examples

The following pharmaceutical composition combining (3S,3S') 4,4'-disulfanediylbis(3-aminobutane 1-sulfonic acid) and enalapril in a weight ratio 50/1 can be prepared for the preparation of therapeutic units. The pharmaceutical composition can be conditioned into glass vials. The powder is extemporaneously reconstituted before oral use with 100 mL of water.

| Components | Ratio 50:1 |
| --- | --- |
| RB150 | 125.00 mg |
| enalapril | 2.50 mg |
| Lactose, anhydrous | 202.70 mg |
| Magnesium stearate | 3.38 mg |
| Silica, dental type | 6.76 mg |
| Total per vial | 340.34 mg |

The pharmaceutical composition can be prepared as followed: RB150 and silica are sieved using a 800 μm screen then are mixed using a X-bag (or equivalent material) during 5 minutes at 3 rpm. Enalapril maleate and the anhydrous lactose is then loaded, and mixing is continued during 10 minutes at 3 rpm with rotation inversion after 5 minutes. Magnesium stearate is loaded and mixing is conducted during 2 minutes at 3 rpm. The vials are filled with a calculated amount of final mix in order to obtain vials containing 125 mg of RB150 and 2.5 mg of enalapril.

Same kind of pharmaceutical compositions comprising RB150 and valsartan can be prepared.

The invention claimed is:

1. A method for treatment of arterial hypertension or indirectly or directly related diseases, wherein said method comprises orally administering to a subject in need of such treatment an effective amount of a combination of (3S,3S') 4,4'-disulfanediylbis(3-aminobutane 1-sulfonic acid) or a pharmaceutically acceptable salt or solvate thereof and enalapril, wherein an hypotensive effect occurs within the first 2 hours after administration of said combination, and wherein the weight ratio of (3S,3S') 4,4'-disulfanediylbis(3-aminobutane 1-sulfonic acid) relative to enalapril is 100/1.

2. The method according to claim 1, wherein the method is for the treatment of heart failure.

3. The method according to claim 1, wherein both active ingredients are coadministered, preferably simultaneously coadministered.

4. The method according to claim 1, wherein the method is for the treatment of arterial hypertension.

* * * * *

UNITED STATES PATENT AND TRADEMARK OFFICE
CERTIFICATE OF CORRECTION

PATENT NO. : 10,959,938 B2
APPLICATION NO. : 14/367408
DATED : March 30, 2021
INVENTOR(S) : Catherine Llorens-Cortes et al.

It is certified that error appears in the above-identified patent and that said Letters Patent is hereby corrected as shown below:

On the Title Page

Item (73), add second Assignee -- INSERM (INSTITUT NATIONAL DE LA SANTÉ ET DE LA RECHERCHE MÉDICALE) --

Item (86), delete "PCT/EP2012/706607" and insert -- PCT/EP2012/076607 --

In the Drawings

Figure 3 (Y axis) delete "MABP" and insert -- ΔMABP --

Figure 4 (Y axis) delete "MABP" and insert -- ΔMABP --

In the Specification

Column 2, Line 2, delete "(GCBs)" and insert -- (CCBs) --

Column 2, Line 37-51, delete "Recent evidences support that a functional RAS, controlling cardiovascular functions and body fluid homeostasis, is also present in the brain (Llorens-Cortes C. and Mendelsohn F A. Organisation and functional role of the brain angiotensin system. J Renin Angiotensin Aldosterone Syst 2002 September; 3 Suppl 1:S39-S48). Hyperactivity of the brain RAS and particularly of aminopeptidase A (APA), a membrane-bound zinc metalloproteases involved in vivo in the conversion of brain angiotensin II (AngII) and to angiotensin III (AngIII) (Zini et al PNAS 1996) respectively, plays a critical role in mediating hypertension in various animal models of hypertension (Marc Y. and Llorens-Cortes C.
The role of the brain renin-angiotensin system in hypertension: Implications for new treatment. Prog Neurobiol. 2011 Jul. 7; 95(2):89-103)." and insert the same on Column 2, Line 38, as a new paragraph Signed and Sealed this
First Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,959,938 B2

Column 2, Lines 52-67, delete "Several studies pointed out that in the brain, AngIII and not Ang II as established at the periphery, constitutes one of the major effector peptides of the brain RAS in the control of BP and AVP release (Zini et al PNAS 1996, Reaux et al PNAS 1999).
Furthermore brain AngIII exerts a tonic stimulatory action on the control of BP in hypertensive animals (Reaux at al PNAS 1999, Fournie-Zaluski et al PNAS 2004). Therefore, brain APA, the enzyme generating AngIII in the brain RAS, constitutes a relevant therapeutic target for treatment of arterial hypertension and centrally active APA inhibitors represent a new class of antihypertensive agents. Among these novel antihypertensive agents, one can cite in particular (3S,3S') 4,4'-disulfanediylbis(3-aminobutane 1-sulfonic acid) that is a prodrug of the selective aminopeptidase A (APA) inhibitor 3-amino 4-mercaptobutanesulfonic acid (also called EC33)." and insert the same on Column 2, Line 51, as a continuation of the same paragraph Column 4, Line 31, delete "palmoic" and insert -- pamoic --

Column 4, Line 34, delete "steroic" and insert -- steroid --

Column 5, Line 62, delete "injec-tions" and insert -- injections --

Column 6, Line 1, delete "su-crose" and insert -- sucrose --

Column 6, Line 17, delete "dis-solving" and insert -- dissolving --

Column 6, Line 46, delete "po-made" and insert -- pomade --

Column 7, Line 60, delete "coadministered" and insert -- co-administered --

Column 7, Line 65, delete "RB150" and insert -- RB150. --

Column 8, Line 22, delete "dose" and insert -- does). --